(12) United States Patent
Meng et al.

(10) Patent No.: US 9,687,844 B2
(45) Date of Patent: Jun. 27, 2017

(54) LIQUID SPECIMEN CUP INCLUDING MOVABLE CADDY AND TRANSLUCENT ADULTERATION PANEL

(71) Applicants: Ellen Q. Meng, San Diego, CA (US); Waiping Ng, San Diego, CA (US)

(72) Inventors: Ellen Q. Meng, San Diego, CA (US); Waiping Ng, San Diego, CA (US)

(73) Assignee: Ellen Meng, San Diego, CA (US)

( * ) Notice: Subject to any disclaimer, the term of this patent is extended or adjusted under 35 U.S.C. 154(b) by 0 days.

(21) Appl. No.: 14/546,375

(22) Filed: Nov. 18, 2014

(65) Prior Publication Data

US 2015/0140681 A1 May 21, 2015

Related U.S. Application Data

(60) Provisional application No. 61/905,755, filed on Nov. 18, 2013, provisional application No. 62/065,419, filed on Oct. 17, 2014.

(51) Int. Cl.
| | |
|---|---|
| *B01L 3/00* | (2006.01) |
| *A61B 10/00* | (2006.01) |
| *B01L 9/00* | (2006.01) |

(52) U.S. Cl.
CPC .......... *B01L 3/5023* (2013.01); *A61B 10/007* (2013.01); *B01L 9/00* (2013.01); *B01L 2200/025* (2013.01); *B01L 2200/141* (2013.01); *B01L 2300/046* (2013.01); *B01L 2300/0609* (2013.01); *B01L 2300/0672* (2013.01); *B01L 2400/0683* (2013.01)

(58) Field of Classification Search
CPC ............. A61B 10/007; B01L 2200/025; B01L 2200/141; B01L 2300/046; B01L 2300/0609; B01L 3/5023
See application file for complete search history.

(56) References Cited

U.S. PATENT DOCUMENTS

| | | | |
|---|---|---|---|
| 5,403,551 A | 4/1995 | Galloway et al. | |
| 5,976,895 A | 11/1999 | Cipkowski | |
| 6,277,646 B1 | 8/2001 | Guirguis et al. | |
| 6,548,019 B1 * | 4/2003 | Lee ..................... | A61B 10/0096 422/417 |
| 6,616,893 B1 * | 9/2003 | Pham ................... | G01N 33/528 422/417 |
| 6,726,879 B2 | 4/2004 | Ng et al. | |

(Continued)

*Primary Examiner* — Sam P Siefke
(74) *Attorney, Agent, or Firm* — Charmasson, Buchaca & Leach, LLP

(57) ABSTRACT

A fluid specimen collection, storage, transport, and testing cup contains a chromatographic strip-carrying caddy which moves between an initial position allowing a deposited liquid specimen to contact the test strips, and a second, sealed position where the strips are hermetically isolated from a remainder portion of the specimen stored for later confirmatory testing. The caddy is moved between the two positions by screwing a threaded lid onto the top opening of the cup. The axial range of the screw is limited by a removable obstruction collar. The caddy can include a liquid specimen containing chamber having a lower opening sealed by a frangible barrier. The strips can be loaded in a cartridge mountable to the caddy. An adulteration panel having a transparent adhesive backed fronting can secure adulteration patches to the caddy.

18 Claims, 12 Drawing Sheets

(56) References Cited

U.S. PATENT DOCUMENTS

| | | | |
|---|---|---|---|
| 2002/0085953 A1* | 7/2002 | Parker | A61B 10/007 422/412 |
| 2003/0007892 A1* | 1/2003 | Smith | G01N 33/528 422/400 |
| 2003/0206829 A1 | 11/2003 | Cui et al. | |
| 2006/0127274 A1* | 6/2006 | Vallejo | A61B 10/007 422/417 |
| 2007/0196234 A1* | 8/2007 | Huff | A61B 10/007 422/400 |
| 2008/0105066 A1* | 5/2008 | Liang | A61B 10/007 73/865.6 |
| 2012/0190122 A1* | 7/2012 | Lin | A61B 10/0096 436/161 |
| 2013/0006146 A1* | 1/2013 | Vemalarajah | A61B 10/007 600/573 |

* cited by examiner

LIQUID SPECIMEN CUP INCLUDING MOVABLE CADDY AND TRANSLUCENT ADULTERATION PANEL

PRIOR APPLICATION

This application claims to benefit of U.S. Provisional Utility Patent Application Ser. No. 61/905,755, filed 2013 Nov. 18, and U.S. Provisional Utility Patent Application Ser. No. 62/065,419, filed 2014 Oct. 17 both of which are incorporated herein by reference.

FIELD OF THE INVENTION

The invention relates to immunoassay devices for conducting chromatographic testing of fluid specimens, and more particularly to devices for collection, preliminary screening, storage, and later confirmatory testing of bodily fluids.

BACKGROUND

Fluid specimen cups are commonly used to collect and test fluid specimens for the presence or absence of specific "indicators" which show the presence of certain chemicals, hormones, antibodies or antigens associated with various physiological conditions and are commonly used for drug screening.

As disclosed in Cipkowski U.S. Pat. No. 5,976,895, preliminary testing or screening is often conducted by manually inserting the bottom end of a cartridge carrying a number of immunoassay-type chromatographic test strips into a cup to contact the liquid specimen with the sample pad on the strips. The use of multiple strips in a single cartridge can simultaneously conduct a panel of tests from a single specimen.

Unfortunately, the results of the test can be affected by the volume of fluid in the sample. In other words, the results in the Cipkowski device can be different depending on whether the cup is returned ⅓ full versus ⅔ full. Greater accuracy can be achieved by requiring the fluid sample to be within a narrow volume range. However, adjusting the volume of the specimen in a device like the one in Cipkowski must be done manually and therefore can be a difficult, time-consuming, and prone to inaccuracy. Such adjustment also carries a health risk for the person conducting the test and a contamination risk to the specimen or testing media.

Oftentimes, if an initial screening test comes back positive for drug use, the conductors of the test may seek to confirm the result by conducting a more rigorous and accurate secondary test in the laboratory. However, conducting the preliminary test using the Cipkowski device may contaminate that part of the specimen exposed to the chemicals carried on the preliminary test strips. In the past, this problem has been addressed by taking multiple separate specimens or being forced to take specimens removed in time from when the original specimen was taken. One can easily appreciate that the taking of a subsequent specimen after a prolonged period allows for changes in the physiology of the test subject. For example, a person suspected of taking drugs can cease drug use whereupon tests taken days later may not turn up positive. In order to avoid taking multiple specimens at potentially far removed times, it is most desirable to perform the confirmatory test on the fluid specimen originally supplied.

Devices such as that disclosed in Ng et al., U.S. Pat. No. 6,726,879 attempt of divide the sample into two separate portions. The first portion is for the preliminary screening test, and the second portion is for securely preserving part of the specimen for transport to a lab for later confirmatory testing. In this way, the first portion can be subjected to the test strips without contaminating the second portion. These devices can be bulky, complicated to operate and costly to manufacture. Manufacturing cost should be kept at a minimum when the device is intended to be disposable.

The device of Guirguis U.S. Pat. No. 6,277,646 provides a movable fluid releasing element which can be driven by the screwing on of the device lid. This allows greater control of the initiation of the preliminary screening test. However, increased manufacturing costs can be expected in forming the frangible wall feature, and using additional components such as the additional bottom wall. Additional costs can be expected because of the detailed and careful assembly required in order to not damage the frangible wall.

In many devices it can be difficult to ensure that the device provides the necessary amount or aliquot of fluid for preliminary testing while also preserving an adequate amount for later confirmatory testing.

The devices disclosed in the above-cited references allow the test to be initiated a time after the placement of the specimen in the cup. Thus a user can control the initiation of the test. Sometimes however it is advantageous to provide a cup where the test is automatically initiated in a non-controlled manner at the time the specimen is deposited. This can result in a device which is less expensive to manufacture and easier to use. The Ng and Guirguis devices for example are not readily adaptable to non-controlled test initiation use.

For many devices used to detect abused drugs, it is desirable to include an adulteration test which typically can include a plural number of colored patches for assessing whether the concentration of certain adulteration parameters such as pH fall outside their acceptable ranges indicating an adulterant may have been added to fool the preliminary test into recording a false negative. Cups which can be readily adapted to include an adulteration test are therefore desirable.

Increasingly, preliminary screening tests are being performed and evaluated by relatively unskilled technicians or even the general public. Therefore, the device needs to be relatively simple to operate to ensure adequate exposure of the preliminary test strips and to provide more consistent results.

Therefore there is a need for a specimen test cup which addresses some or all of the above identified inadequacies.

SUMMARY

The principal and secondary objects of the invention are to help provide an improved fluid specimen collection device. These and other objects are achieved by a vessel having a lid-actuated moveable strip-carrying caddy.

In some embodiments there is provided an assay device for testing a fluid specimen, said device comprises: a vessel defining a first compartment having a top opening and a closed bottom separated along an axis, and said compartment having a given capacity; wherein said vessel comprises a translucent wall portion having an inner surface; a caddy contained within said compartment, said caddy adapted to mount a number of chromatographic test strips; at least one sealable aperture exposing said strips to said compartment; said caddy being axially translatable within said compartment between a first axial position wherein said aperture is unsealed and a second axial position wherein said aperture is hermetically sealed; a disableable obstruction preventing movement of said caddy between said first and second axial positions; and, a lid removably and hermetically sealing said top opening while said caddy is in either said first or second axial position.

In some embodiments there is provided in an immunoassay flow testing device having a fluid specimen carrying cup sealable by a lid, and a chromatographic testing strip carrying caddy, an improvement which comprises: said caddy being moveable between said first pre-test position and said second post-test position; said lid sealing said cup in said first pre-test position and in said second post-test position; wherein said lid comprises an annular prominence axially bearing against said caddy to drive it axially between said positions.

In some embodiments there is provided a method for conducting a preliminary fluid specimen test and a secondary confirmatory test from a single fluid specimen, said method comprises: locating a chromatographic strip-carrying caddy at a first pre-test axial position within a compartment of a sealable cup; introducing a fluid specimen into said compartment; preliminarily sealing said cup with said lid against a removable obstruction; removing said lid; removing said removable obstruction; resealing said cup with said lid; wherein said resealing comprises: automatically driving said caddy from said first position to a second post-test position, wherein said second position seals an amount of said specimen apart from a volume of said specimen remaining in said cup; observing a result on one or more strips carried in said caddy; removing said resealed lid from said cup after said observing; and, conducting said secondary confirmatory test from said separate volume.

In some embodiments there is provided in an assay device for testing a fluid specimen, said device comprises: a vessel defining a first compartment having a top opening and a closed bottom separated along an axis, and said compartment having a given capacity; wherein said vessel comprises a translucent wall portion having an inner surface; a caddy contained within said compartment, said caddy adapted to mount a number of chromatographic test strips; at least one sealable aperture exposing said strips to said compartment; said caddy being axially translatable within said compartment between a first axial position wherein said aperture is unsealed and a second axial position wherein said aperture is hermetically sealed; a disableable obstruction preventing movement of said caddy between said first and second axial positions; and, a lid removably and hermetically sealing said top opening while said caddy is in either said first or second axial position.

In some embodiments a lower lip of said caddy is suspended a distance above said closed bottom while said caddy is in said first position.

In some embodiments said caddy further comprises: an internal chamber having an upper opening and a lower opening; wherein said lower opening is sealed by a frangible barrier.

In some embodiments said device further comprises a projection extending from said closed bottom; said projection being oriented to break said frangible barrier when said caddy is in said second axial position.

In some embodiments said strips are carried within a cartridge insertable in a cavity on said caddy.

In some embodiments said lid comprises an arcuate bearing surface contacting and driving said caddy from said first axial position to said second axial position in correspondence to said lid moving axially said distance.

In some embodiments arcuate bearing surface comprises a resilient washer hermetically sealing a contact between said arcuate bearing surface and said caddy.

In some embodiments an axial distance between said first and second position is between about 3 and 5 millimeter.

In some embodiments the device further comprises an O-ring between said caddy and said vessel for preventing fluid leaking between said channels and said compartment.

In some embodiments said O-ring is dimensioned to support the weight of said caddy in said first position.

In some embodiments said lid is shaped and dimensioned to releasably seal said opening and have an annular prominence shaped and dimensioned to be bearingly engage a brim of said caddy.

In some embodiments said annular prominence is further shaped and dimensioned to contact said caddy in an angularly sliding manner and drive it from said first position to said second position while said lid is being screwed completely on said device.

In some embodiments said caddy is in substantial axial alignment with said compartment.

In some embodiments said device further comprises a guide structure restricting angular movement while allowing axial movement between said caddy and said vessel.

In some embodiments each of said strips is loaded into an empty one of said number of channels within said caddy.

In some embodiments said disableable obstruction comprises a cylindrical collar removably positioned on said vessel to prevent axial movement of said lid beyond a defined limit.

In some embodiments said collar and said lid are co-helically threaded.

In some embodiments said device further comprises: a resilient mat located at said closed bottom of said vessel, said mat being shaped and dimensioned to sealably contact an annular undersurface of said caddy proximate said lower aperture.

In some embodiments there is provided in an immunoassay flow testing device having a fluid specimen carrying cup sealable by a lid, and a chromatographic testing strip carrying caddy, an improvement which comprises: said caddy being moveable between said first pre-test position and said second post-test position; said lid sealing said cup in said first pre-test position and in said second post-test position; wherein said lid comprises an annular prominence axially bearing against said caddy to drive it axially between said positions.

In some embodiments there is provided a method for conducting a preliminary fluid specimen test and a secondary confirmatory test from a single fluid specimen, said method comprises: locating a chromatographic strip-carrying caddy at a first pre-test axial position within a compartment of a sealable cup; introducing a fluid specimen into said compartment; preliminarily sealing said cup with said lid against a removable obstruction; removing said lid; removing said removable obstruction; resealing said cup with said lid; wherein said resealing comprises: automatically driving said caddy from said first position to a second post-test position, wherein said second position seals an amount of said specimen apart from a volume of said specimen remaining in said cup; observing a result on one or more strips carried in said caddy; removing said resealed lid from said cup after said observing; and, conducting said secondary confirmatory test from said separate volume.

In some embodiments there is provided in a liquid specimen adulteration test panel including a plurality of individual detector patches each adapted to detect in said liquid specimen an adulteration parameter, an improvement which comprises: a fronting made from a strip of translucent sheet material; a layer of adhesive secured to a first face of said strip; said layer of adhesive contacting and holding said patches onto said first face; said patches being spaced apart from one another to align with spaced apart separate wells on a chromatographic strip carrying cartridge; and, wherein portions of said adhesive exposed between said patches contacts ribs separating said wells.

In some embodiments said cartridge comprises an arcuate body adpated to be mounted upon a movable caddy slidingly mounted to a liquid specimen cup.

In some embodiments said cartridge comprises a hand graspable body for manual dipping into a liquid specimen cup.

The original text of the original claims is incorporated herein by reference as describing features in some embodiments.

DESCRIPTION OF THE EXEMPLARY EMBODIMENTS

Figure 1:
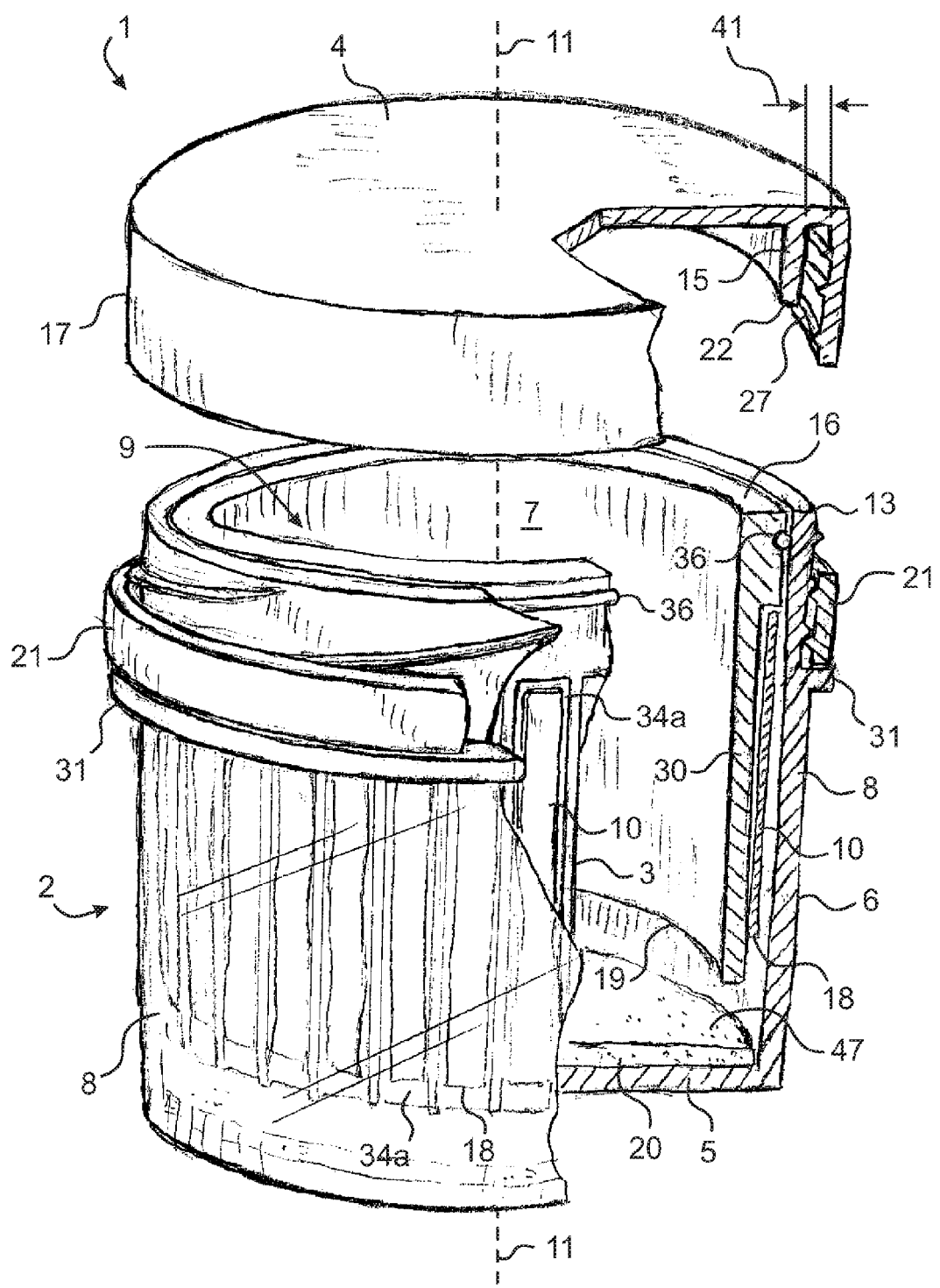
FIG. 1 is a diagrammatic, partial cut-away, partial cross-sectional, perspective view of an assembled testing cup according to an exemplary embodiment of the invention.

Referring now to the drawing there is shown in FIG. 1 a fluid specimen collection, testing, transport, and storage device 1 for preliminarily screening of a fluid specimen such as urine for the presence of disease or abused drugs and saving a separate amount of that specimen for later confirmatory testing. The device can include a generally cylindrical container vessel 2 having a central axis 11, a top upper lip 13 surrounding a top circular opening 9 releasably sealable by a threaded circular lid 4, a circular base 5, and a generally cylindrical sidewall 6 enclosing a substantially cylindrical internal compartment 7. The vessel can be made of a translucent material so that the sidewall forms a window 8 through which is viewed an axially movable caddy 3 mounting a number of chromatographic test strips 10 from which results of the preliminary screening can be determined while the compartment remains sealed. The lid has an internal annular prominence 15 which bears against the upper brim 16 of the caddy. As the lid is screwed onto the vessel, it drives the caddy from a first upper position where the bottom ends 18 of the strips are exposed to the compartment, down to a second lower position so that the lower lip 19 of the caddy contacts a circular resilient mat 20 supported by the base 5. When the caddy is in its second, lower position the mat seals the strips from the remainder of the specimen in the compartment. A removable threaded collar 21 supported by a flange 31 on the vessel prevents the lid from moving the caddy until the collar is removed. The vessel, lid and caddy are made from a substantially rigid, durable, fluid impermeable material such as such as substantially clear polyethylene plastic. These features will be described in greater detail below.

Figure 2:
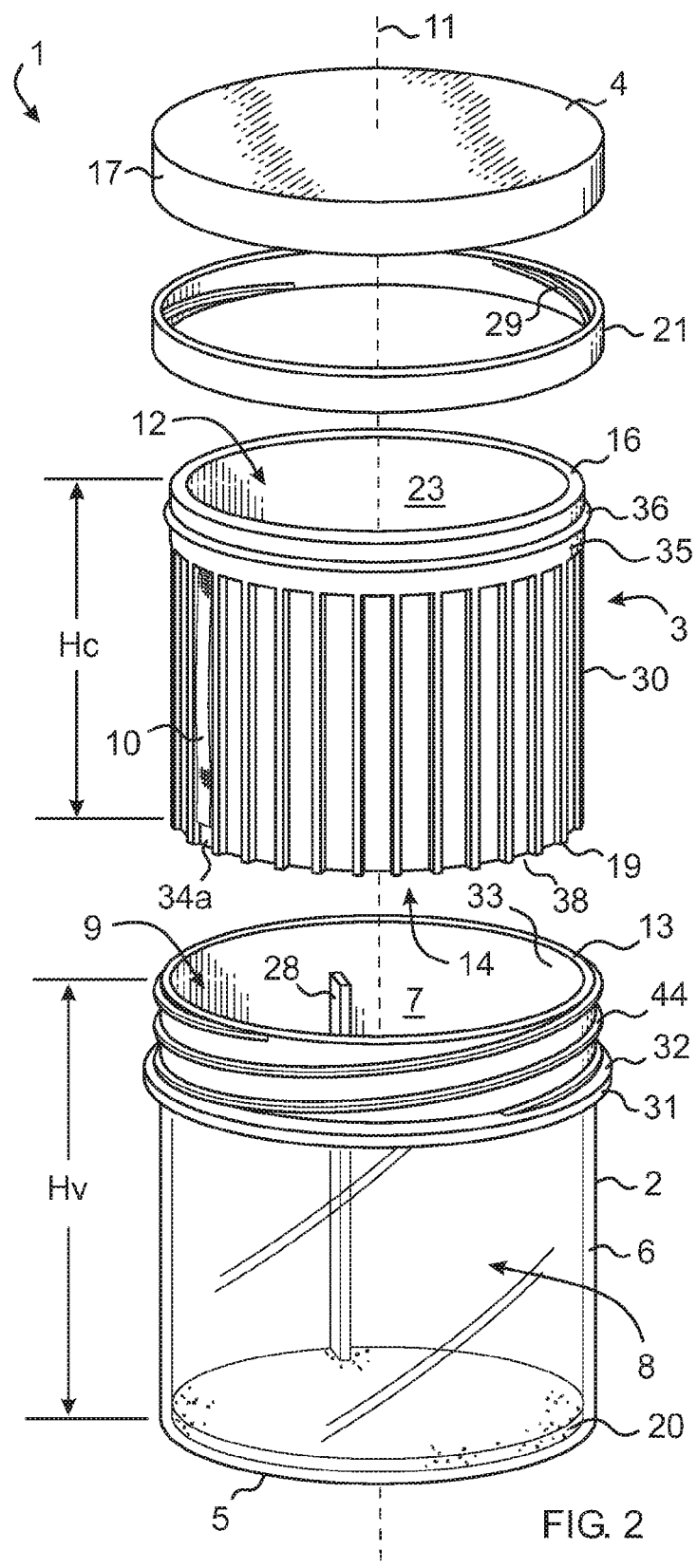
FIG. 2 is a diagrammatic, exploded, perspective view of the testing cup of FIG. 1.
Figure 3:
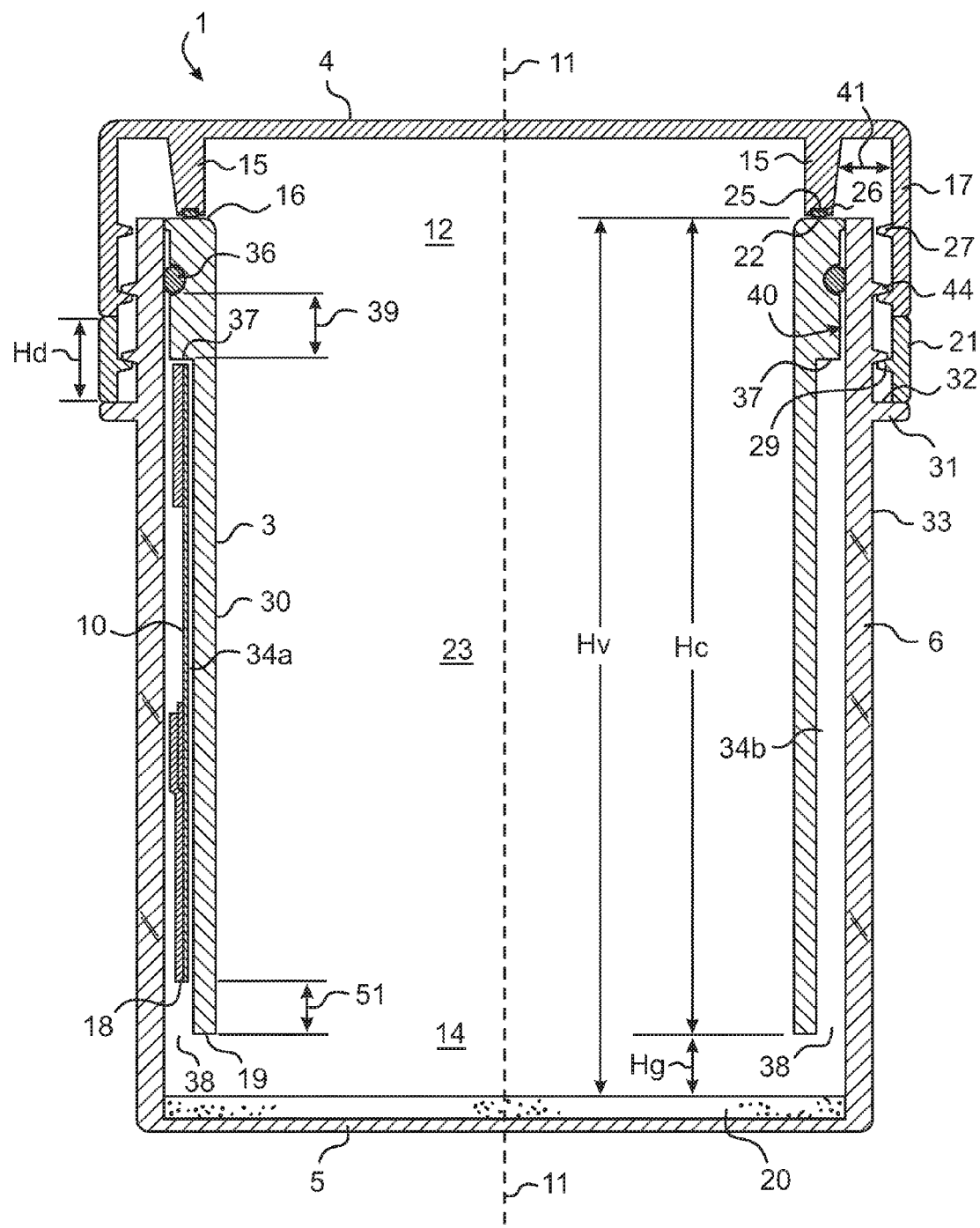
FIG. 3 is a diagrammatic cross-sectional side view of the cup of FIG. 1.

Referring now to FIGS. 1-3, the strip-carrying caddy 3 can include a hollow substantially cylindrical body 30 having an upper opening 12 surrounded by a substantially circular upper brim 16 leading to a substantially cylindrical internal chamber 23 terminating at an opposite lower opening 14 surrounded by substantially circular lower lip 19. A number of substantially parallel, angularly spaced apart axially oblong channels 34a,34b can be formed into the substantially cylindrical outer surface 35 of the body which is commensurate with the substantially cylindrical inner surface 33 of the vessel. Each channel can be shaped, dimensioned and oriented to carry a chromatographic test strip 10 so that it can be viewed through the translucent sidewall 6 of the vessel 2. In FIG. 3, the channel 34a is shown carrying a strip while the channel 34b is shown empty for comparison. Each channel can have a closed top end 37 and an open bottom end which forms an aperture 38 through which an amount of fluid specimen may pass in order to initiate the preliminary screening test by soaking into the bottom pad portions of the strips.

The height of the channels 34a,34b can be selected to form a separation depth 51 between the bottom ends 18 of the strips 10 and the lower lip 19 of the caddy 3. In this way the level of the fluid specimen can be kept away from contacting the bottoms ends of the strips by the air pocket trapped in the channels until the pressure in the compartment is increased thus forcing specimen up the channels to contact the strips. For a cup having a volume of between about 100 and 150 milliliter, the depth is preferably between about 3 millimeter and about 10 millimeter, and for most applications preferably between about 3 millimeter and about 5 millimeter.

Alternately, if immediate initiation of the test is desired upon placement of the specimen in the cup, the bottom ends 18 of the strips 10 can be located commensurate with the lower lip 19 of the caddy 3 so that the separation depth 51 is essentially zero.

The caddy 3 can be mounted substantially coaxially within the internal compartment 7. The caddy has a shorter maximum axial dimension Hc than the axial dimension Hv of the compartment so that it can be positioned in a first, pre-test position as shown in FIGS. 1 and 3, where its circular lower lip 19 is suspended an axial distance Hg from the upper inner surface 47 of the mat 20 forming the closed bottom of the compartment. In this way the bottom apertures 38 of the strip-carrying channels are exposed to the internal compartment and liquid specimen once the specimen has been deposited.

The lid 4 has a downwardly projecting cylindrical skirt 17 having internal threads 27 shaped, dimensioned and located to threadingly engage corresponding outwardly threaded 44 vessel sidewall 6 near the upper lip 13 surrounding its top opening 9. The lid also has a coaxial annular prominence 15 spaced radially inwardly apart from the skirt to form a gap 41 in order to accommodate passage of vessel upper lip therebetween. The prominence provides an annular bearing surface 22 shaped, dimensioned and oriented to bearingly press against the circular upper brim 16 of the caddy and force it slidingly downwardly relative to the vessel 2 along a smooth inner surface portion 40 of its sidewall from its first upper axial position shown in FIG. 3 to its second lower axial position shown in FIG. 9 when the lid is threadingly engaged and screwed completely upon the vessel. The annular bearing surface can be formed by an annular washer 25 carried within a groove 26 cut into the annular prominence. The washer can be made from a resiliently compressible material such as rubber to help hermetically seal the annular bearing surface against the upper brim of the caddy so that the compartment is hermetically sealed when the caddy is in either its upper or lower position. A guide structure in the form of a vertical tongue 28 inwardly extending from the inner surface of the vessel is dimensioned to intimately and slidingly engage a corresponding vertical groove (not shown) formed into the outer surface of the caddy. The guide structure prevents angular movement of the caddy with respect to the vessel and helps prevent jams between the caddy and vessel. The top terminus of the tongue and groove occur an axial distance below the top upper lip 13 of the vessel and the upper brim 16 of the caddy to accommodate maintaining an upper seal between the caddy and vessel described below.

A dual function O-ring 36 can course circumferentially around the outer surface 35 of the caddy body 30 near its upper brim 16, spaced an axial distance 39 above the closed top ends 37 of the strip-carrying channels 34a,34b. First, the O-ring provides enhanced friction between the caddy and vessel so that the caddy is axially immobilized under its own weight. Second, the O-ring hermetically seals the caddy to the inner surface 40 of the vessel sidewall while allowing axial movement of the caddy with respect to the sidewall. In this way the air in the channels is trapped when liquid has flowed onto the pads of the strips. The trapped air substantially maintains its pressure in order that the flow onto the strip pads is primarily through wicking action. This ensures that the strips do not become saturated with liquid specimen potentially reducing the accuracy of the test being carried out on the strip.

A circumferential flange 31 extends radially outwardly from an outer surface of the cylindrical sidewall 6 of the vessel at an axially medial location. The flange forms an upwardly facing circular ledge 32 for bearing against a removable cylindrical collar 21. The presence of the collar acts as a removable obstruction to axial movement of the lid beyond a limit defined by the axial height Hd of the collar. Once the collar has been removed, the replaced lid can proceed axially beyond the limit. The inner surface of the collar can have a thread 29 shaped, dimensioned and located to screw onto the threads 44 of the lip of the vessel. Thus the thread on the collar and the thread on the lid are co-helical. Alternately, an un-threaded collar can be used. The advantages of an un-threaded collar is its simple hollow cylinder shape which can be manufactured less expensively, and can be more simply and automatedly installed onto the flange of the vessel, and can be removed more quickly by simply lifting without twisting. One disadvantage of an un-threaded collar is that it can be more prone to falling off unintentionally.

Figure 9:
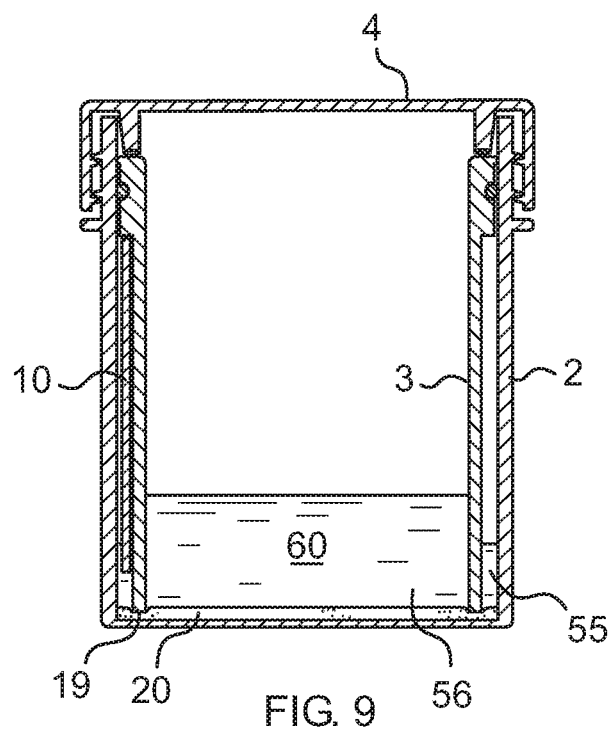
FIG. 9 is a diagrammatic cross-sectional side view of the cup where the lid is completely screwed down upon a collarless cup sealing the confirmatory portion of the specimen from the strips.

As shown in FIG. 9, once the seal has been made between the lower lip 19 of the caddy 3 and bottom mat 20, the single specimen 60 delivered by the donor has been divided into two separate portions 55,56. The first portion 55 is a metered volume portion of specimen fluid contained in the channels. The second portion 56 is the confirmatory portion. Because of the finite capacity of the channels, the volume of the sample contained therein is confidently within a narrower range. This allows the donor to supply a greater range of total specimen volumes while still providing an adequate amount for a reasonably accurate preliminary test.

The collar 21 can be color-coded or otherwise adapted to act as an indicator specifying the type of test panel being run. The lack of the collar also acts as a clear indicator to the technician that the confirmatory portion has been sealed apart from the strips, and that the cup may be handled accordingly.

The preliminary screening test using the above described device can easily be conducted by less skilled workers or even the general public. Thus the device can be sold commercially in drug stores and be available to a much wider market.

Referring now to FIGS. 4-9 there will be described the method of conducting a preliminary screening test and preserving an aliquot of liquid specimen for later confirmatory testing using the device of FIGS. 1-3.

Figure 4:
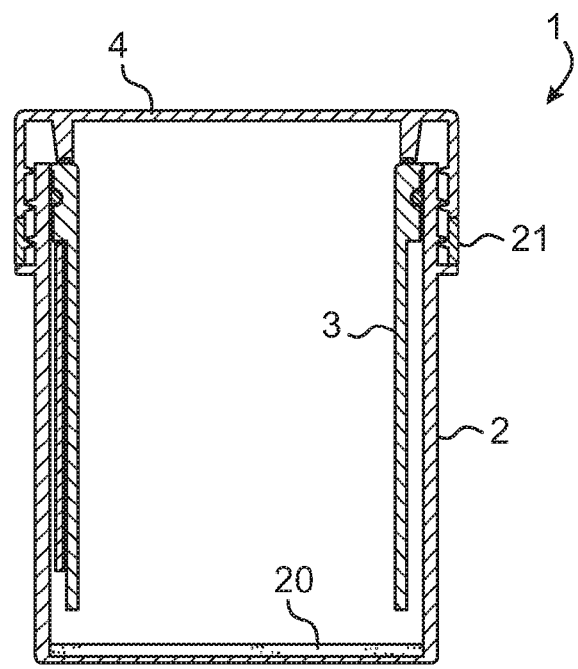
FIG. 4 is a diagrammatic cross-sectional side view of the cup of FIG. 1 as it is handed to a donor.

As shown in FIG. 4, the device 1 can be delivered empty to the donor similarly to a standard lidded cup where the lid 4 is screwingly attached to the vessel 2. It shall be noted that the contained caddy 3 is located in its first, upper position a distance above the mat 20.

Figure 5:
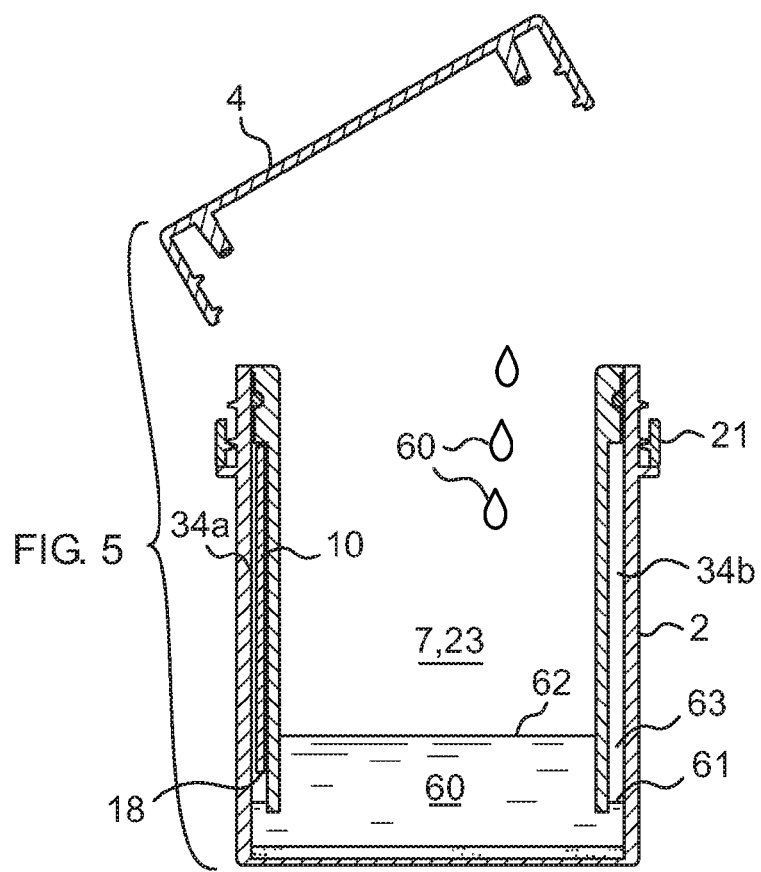
FIG. 5 is a diagrammatic cross-sectional side view of the cup of FIG. 4 having its lid removed and a liquid specimen deposited therein.

As shown in FIG. 5, the donor can remove the lid 4 and leave the collar 21 in place on the vessel 2, and deposit a fluid specimen 60 into the internal chamber 23 of the caddy within the internal compartment 7 of the vessel. It shall be noted that the surface level 61 of the liquid specimen in the channels 34*a*,34*b* is kept lower than the surface level 62 of the liquid specimen in the center of the compartment. This is due to the pressure of the air pocket 63 trapped in the channels above the surface level 61 of the liquid specimen in the channels. This air pocket also prevents the level from reaching the bottoms 18 of the strips 10.

Figure 6:
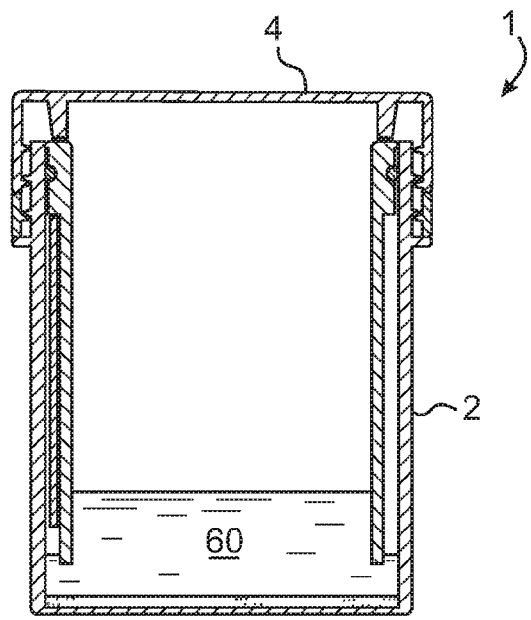
FIG. 6 is a diagrammatic cross-sectional side view of the cup of FIG. 5 where the lid has been secured thereon after the fluid specimen has been deposited therein.

As shown in FIG. 6, the donor can replace the lid 4, and return the cup 1 containing the specimen 60 to the technician. It is important to note that as far as the donor is concerned the process for collecting the specimen has been no different from depositing a specimen in an ordinary lidded cup, thus keeping the process simple for the untrained. Depending on the dimensioning of the strips and channels, the onset of preliminary screening can be prevented by the trapped air pocket 63 in the channels so that the level of the specimen is kept below the bottom ends of the strips. Care should be taken not to tilt the cup from vertical.

Figure 7:
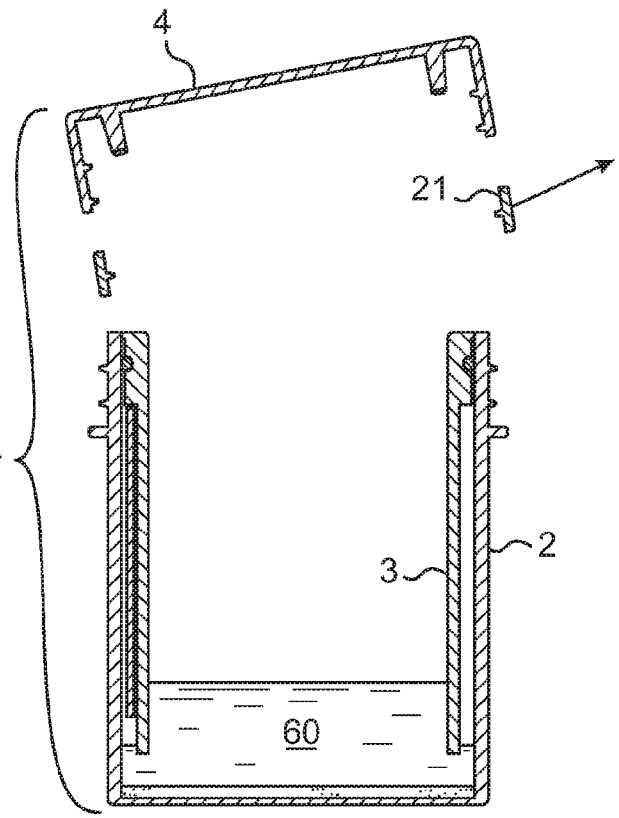
FIG. 7 is a diagrammatic cross-sectional side view of the cup of FIG. 6 where the lid and collar have been removed.

As shown in FIG. 7, in order to begin the preliminary screening test, or as the case may be, if the test has already begun, to seal a portion of fluid specimen apart from the strips for later confirmatory testing, the lab technician can remove the lid 4 and collar 21 from the vessel 2 by unscrewing them. Note that at this point, the caddy 3 remains in its first, upper position.

Figure 8:
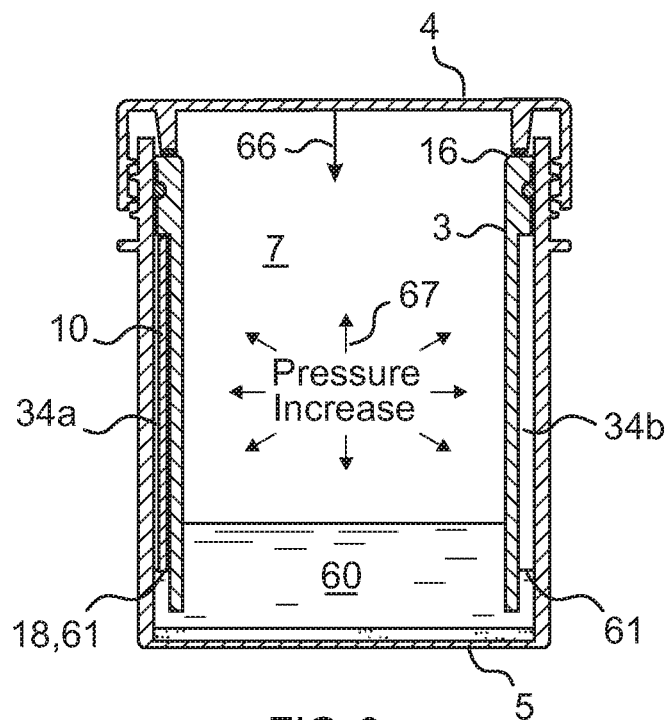
FIG. 8 is a diagrammatic cross-sectional side view of the cup of FIG. 7 where the lid is in the process of being screwed down upon a collarless cup and the preliminary screening has initiated.

As shown in FIG. 8, the lab technician can place the lid 4 back on the vessel 2 and begin screwing it down thus hermetically sealing the lid to the caddy brim 16, and moving the lid axially downward 66 toward the base 5 of the vessel. This action reduces the volume of the internal compartment 7 increasing the internal pressure 67 within the compartment and driving the surface level 61 of the liquid specimen 60 in the channels 34*a*,34*b* upward to contact the bottoms 18 of the strips 10 while the strips themselves are being lowered along with the caddy 3.

As shown in FIG. 9, the lab technician completes screwing the lid 4 onto the vessel 2 driving the inner caddy 3 down to its second lower position to seal its lower lip 19 against the internal compressible mat 20, thus sealing the liquid 60 in the compartment from liquid contacting the strips 10. The cup can than be stored and/or transported for later confirmatory testing.

An advantage of the present embodiment is that it can be manufactured to accommodate a large number strips even though the device may ultimately be loaded with fewer than that large number. The amount of fluid provided to each strip will be essentially the same whether there is one strip or the entire 360 degrees of the perimeter of the caddy is loaded with strips. In addition, the device can be manufactured as both an immediate initiation device and a technician-controlled initiation device, where the difference is only where the bottom ends of the strips are located with respect to the aperture.

Figure 10:
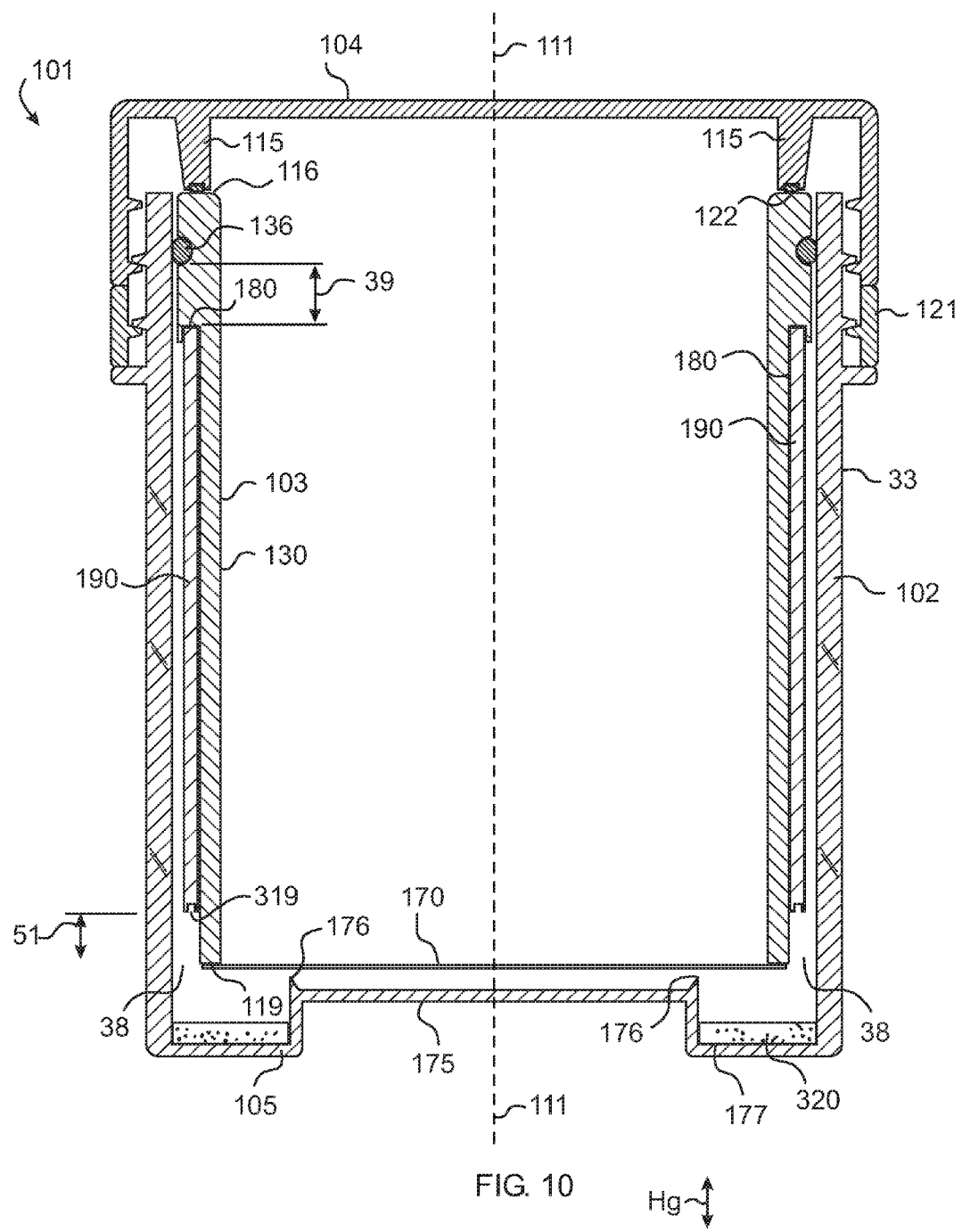
FIG. 10 is a diagrammatic, cross-sectional side view of an assembled testing cup according to an alternate exemplary embodiment of the invention where the caddy includes an outer cavity for mounting a strip-carrying cartridge and a bottom frangible barrier.

Referring now to FIG. 10, there is shown an alternate embodiment of a testing cup 101 similar to the embodiment of FIGS. 1-3 but which provides greater flexibility of the type test being conducted, and greater control over the initiation of the test.

Similarly to the previous embodiment, the cup 101 includes a generally cylindrical container vessel 102 having a substantially circular top opening and a substantially circular base 105 forming a substantially cylindrical internal compartment dimensioned to carry a caddy 103 which can have a substantially hollow cylindrical body 130 having an upper opening surrounded by an upper brim 116 and an opposite substantially circular lower opening 112 surrounded by a lower lip 119 openably sealed by a frangible barrier 170, and an outer cavity 180 for mounting a strip-carrying cartridge 190.

Figure 14:
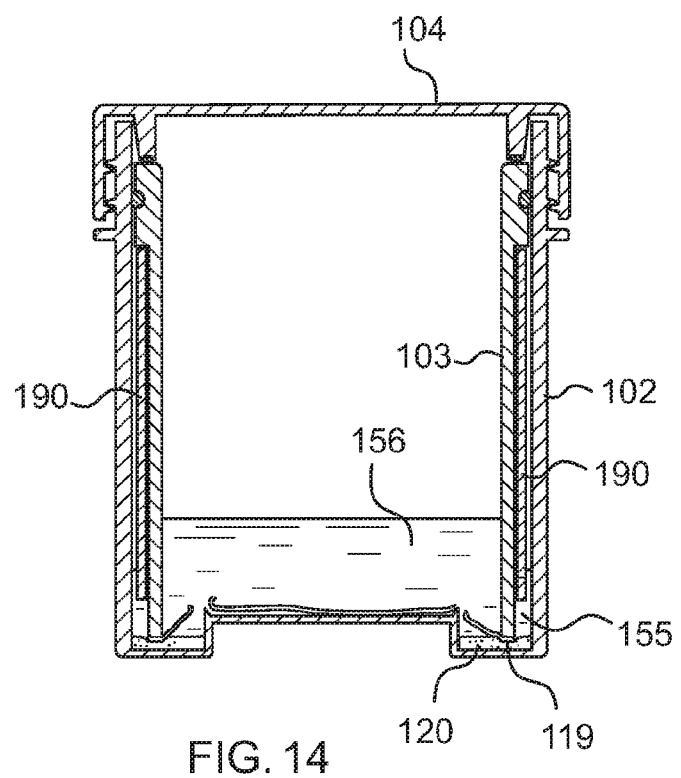
FIG. 14 is a diagrammatic cross-sectional side view of the cup of FIG. 13 where the lid is completely screwed down upon a collarless cup sealing the confirmatory portion of the specimen from the strips.
Figure 16:
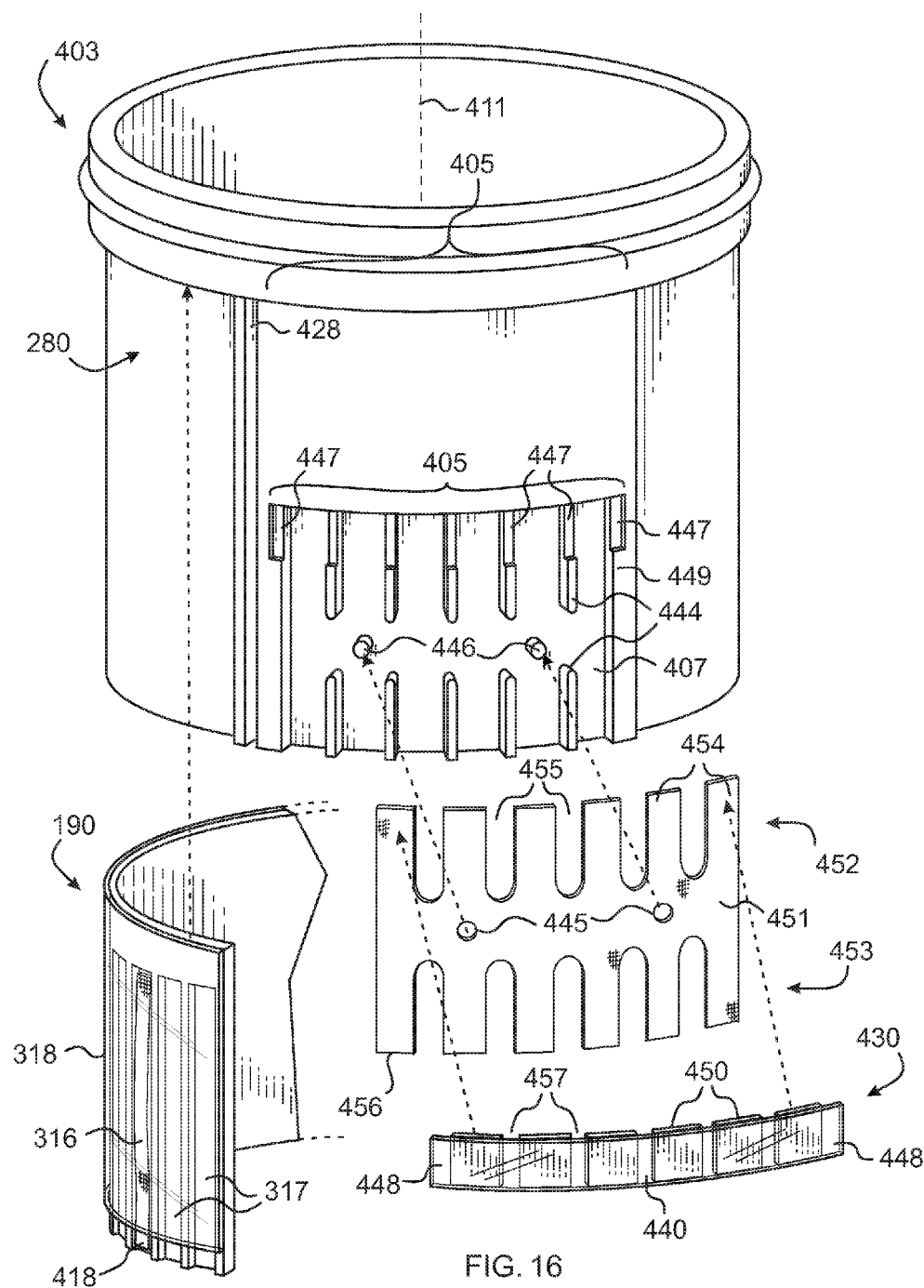
FIG. 16 is a diagrammatic, exploded, partial perspective view of an alternate embodiment of the cup including an adaptation for an alternate adulteration-type test, and an insertable strip-carrying cartridge into the caddy.

The caddy 103 is axially movable with respect to the vessel 102 along a central axis 111 between an upper position as shown in FIG. 10 to a lower position as shown in FIG. 14. The caddy can have an outer cavity 180 for mounting a removable cartridge 190. FIG. 16 shows that such a cartridge can be preloaded with a plural number of chromatographic test strips 316 each within a dedicated axially oblong channel 317 behind a transparent outer sidewall 318. Holes 319 in the bottom of the cartridge allow liquid to pass through to the strips. In this way, the cup can be readily adapted to performing a different type of test. For example, the cup can be easily converted from a disease detection test to an abused drugs detection test by simply swapping a first cartridge containing a panel of disease-related strips to a second cartridge containing a panel of abused drugs detecting strips.

The caddy 103 can include a substantially circular frangible barrier 170 made from a breakable sheet material such as plastic membrane-backed foil sealed along the circumference of the lower lip 119 by an adhesive or through other well-known means. The barrier allows the initial deposit of the specimen to be kept from contacting the strips until the barrier is broken. The barrier is oriented substantially perpendicular to the axis 111 so that it can be broken by the penetration of a projection 175, shaped, dimensioned and oriented to extend upwardly from the center portion of the bottom 105 of the vessel, when the caddy moves to its lower position. One or more spikes 176 on the projection facilitate easy rupturing of the barrier membrane. While the caddy is located in its upper location, the lower opening 112 sealed by the barrier 170 of the caddy remains suspended over the projection.

The projection 175 also forms a circumferential moat 177 on the bottom of the vessel 102 which can carry a ring-shaped washer forming a resilient mat 120 which can seal against the lower lip 119 of the caddy in its lower position, thus sealing off the specimen remaining in the caddy's internal compartment 107 for later confirmatory testing.

The caddy is moved from its upper position to its lower position in the same manner as provided in the embodiment of FIGS. 1-3, where the lid 104 has a coaxial annular prominence 115 providing an annular bearing surface 122 shaped, dimensioned and oriented to bearingly press against the circular upper brim 116 of the caddy and force it slidingly downwardly relative to the vessel 102 as the lid 104 is screwed into place in the absence of the obstructing collar 121.

A dual function O-ring 136 can course circumferentially around the cylindrical outer surface of the caddy body 130 near its upper brim 116 enhancing friction between the caddy and the vessel so that the caddy is axially immobilized under its own weight and the weight of a specimen contained in the chamber, and hermetically sealing the caddy to the vessel while allowing forced axial movement of the caddy with respect to the vessel. This prevents liquid specimen from seeping out of the space formed between the outer surface of the caddy body and the inner surface of the vessel.

Figure 11:
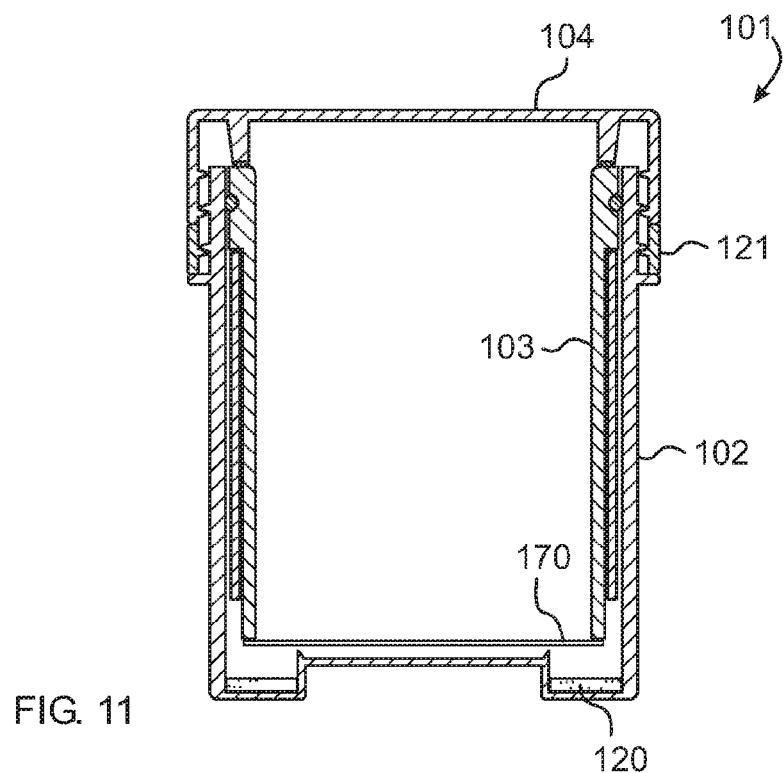
FIG. 11 is a diagrammatic cross-sectional side view of the cup of FIG. 10 as it is handed to a donor.

As shown in FIG. 11, the device 101 can be delivered empty to the donor similarly to a standard lidded cup where the lid 104 is screwingly attached to the vessel 102. It shall be noted that the contained caddy 103 mounts the strip-carrying cartridge 190 and is located in its first, upper position a distance above the mat 120 with the frangible barrier 170 intact.

Figure 12:
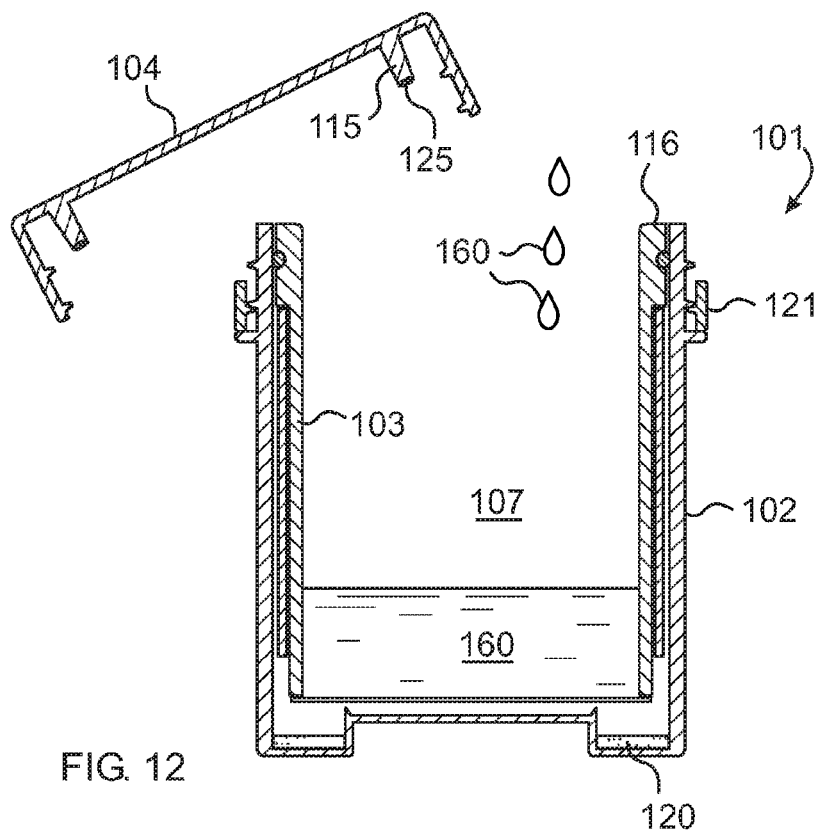
FIG. 12 is a diagrammatic cross-sectional side view of the cup of FIG. 11 having its lid removed and a liquid specimen deposited therein.

Referring to FIG. 12, the donor can remove the lid 104 and leave the obstructing collar 121 in place on the vessel 102, and deposit a fluid specimen 160 into the internal chamber 107. Once the lid is replaced, the specimen is sealed within the internal chamber of the caddy 103 by the intact frangible barrier 170 and the washer 125 between the lid annular prominence 115 and the upper brim 116 of the caddy, and the cup is ready for storage and/or transport in an uninitiated condition.

Figure 13:
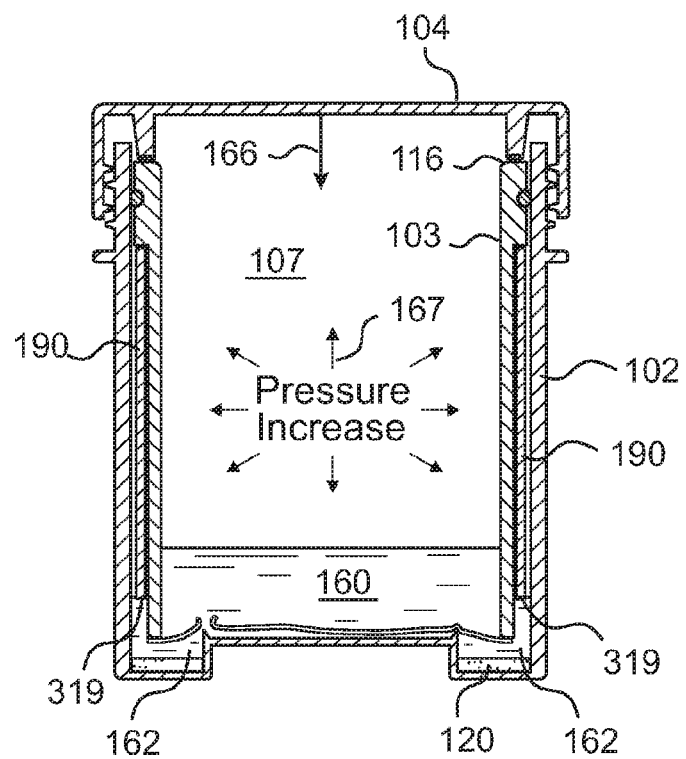
FIG. 13 is a diagrammatic cross-sectional side view of the cup of FIG. 12 where the lid is in the process of being screwed down upon a collarless cup, the frangible barrier broken, and the preliminary screening has initiated.

Referring to FIG. 13, after the lab technician has removed the lid 104 and the obstructing collar, she can replace the lid 104 back on the vessel 102 and begin screwing it down thus hermetically sealing the lid to the upper brim 116 of the caddy 103, and moving the lid axially downward 166. This action forces the frangible barrier 170 against the spikes of the projection 175 extending upwardly from the base of the vessel, thereby rupturing the barrier, and allowing an amount 162 of the liquid specimen 160 to flow out of the internal compartment 107 of the caddy and into the space between the vessel and caddy and enter through the holes 319 of the cartridge 190 to contact the strips to initiate preliminary screening. This action also reduces the volume of the internal compartment 107 increasing the internal pressure 167 within the compartment which helps to drive an amount 162 of liquid specimen out of the chamber of the caddy once the barrier has been broken.

Referring to FIG. 14, the lab technician completes screwing the lid 104 onto the vessel 102 driving the inner caddy 103 down to its second lower position to seal its lower lip 119 against the internal compressible mat 120, thus sealing the liquid 156 in the compartment from liquid 155 contacting the cartridge 190. The cup can than be stored and/or transported for later confirmatory testing.

An advantage of the present embodiment is that it too can be manufactured to accommodate a large number strips even though the device may ultimately be loaded with fewer than that large number. The amount of fluid provided to each strip will be essentially the same whether there is one strip or the entire 360 degrees of the perimeter of the caddy is loaded with strips. Also, cartridges containing different panels of strips can be easily swapped into the caddy to change the type of test being conducted. In addition, the device can be manufactured as both an immediate initiation device and a technician-controlled initiation device, where the difference is only the presence of the frangible barrier and the location of the bottoms of the strips.

Figure 15:
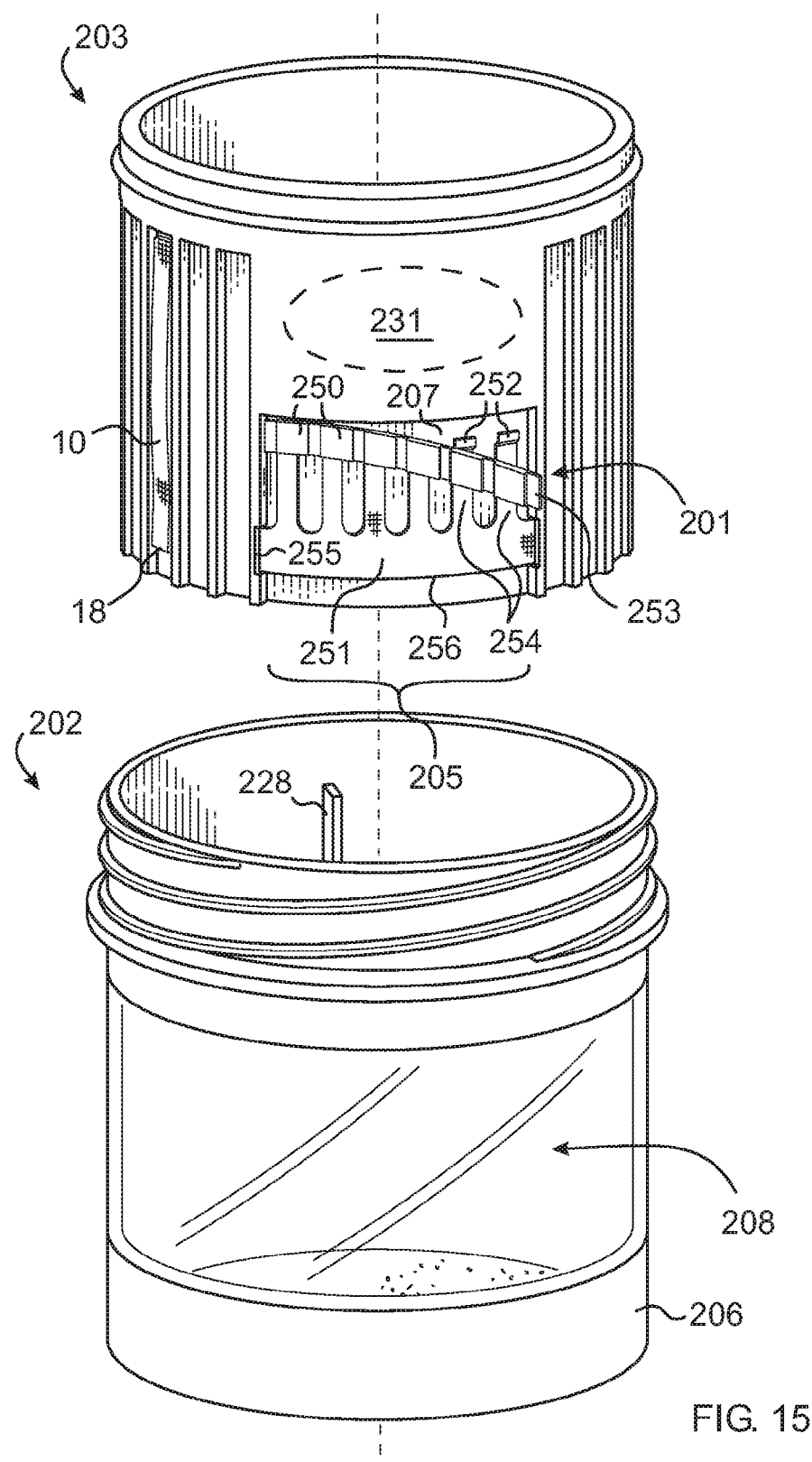
FIG. 15 is a diagrammatic, exploded, partial perspective view of an alternate embodiment of the cup including an adaptation for an adulteration-type test, and a limited coverage translucent viewing window.

Alternately, the entire 360 degree perimeter of the caddy need not contain channels for strips. As shown in FIG. 15, an angular portion 205 of the perimeter of the caddy 203 can be manufactured to have a recess 207 accommodate insertion of an adulteration test device 201. Further, the sidewall 206 of the vessel 202 can be made from an opaque material and a translucent window 208 provided.

The adulteration test apparatus 201 can use a plural number of colored patches 250 supported on a porous backing 253 for testing the pH of the specimen to determine whether an adulterant may have been added to fool the preliminary test into recording a false negative. In order to ensure the patches are not immersed in liquid, a wicking structure 251 can be used to contact specimen along a lower edge 256 positioned at the same axial height as the bottoms 18 of the strips 10. Liquid wicks upwardly through spaced apart wicking columns 254 leading to upper contacts 252 contacting the patches 250. Lateral tabs 255 on the wicking structure engage corresponding lateral wells in the vertical borders of the recess 207 to secure the adulteration test within the recess.

Use of an adulteration test which is axially shorter than a mounted strip frees up a space 231 of the caddy which can carry instruction, a manufacturers logo or other information.

Alternatively, as shown in FIG. 16, an angular portion 405 of the perimeter of the caddy 403 can be manufactured to have a recess 407 to accommodate insertion of an alternate adulteration test apparatus including an alternate adulteration testing panel 430 having a number of colored patches 450 attached to a translucent fronting 440 made from a clear film of plastic. A pH compatible adhesive can be used to attach the patches to the fronting.

A dual comb-shaped wicking structure 451 made from a compatible porous material such as nitrocellulose can be used to contact the specimen along a lower edge 456 positioned at the same axial height as the bottoms 418 of strips 316 carried within an insertable cartridge 190. Separator ribs 444 and registration pins 446 within the recess are located to uniquely engage the spaces 455 between corresponding spaced apart wicking columns 454 and registration perforations 445 in the wicking structure to assure the proper positioning of the wicking structure within the recess. The wicking columns are divided into upper and lower rows 452,453 where each column in the upper row contacts a dedicated one of the patches 450. The columns and separator ribs help prevent chemicals on one patch from contaminating a neighboring patch. The columns also help reduce the amount of liquid necessary to saturate the wicking structure while still proving an easily manufactured unitary wicking structure which is easily assembled with the caddy. The wicking structure can be both laterally symmetric and vertically symmetric so that the structure can be flipped or rotated 180 degrees and remain properly oriented for insertion into the recess. Indentations 447 in the upper portions of the separator ribs and in the vertical borders 449 of the recess are oriented and dimensioned to engage the adhesive coated interstices 457 and lateral flaps 448 on the fronting engage to secure the adulteration test within the recess and properly locate the patches with respect to the wicking structure. The indentations are slightly shallower than the recess to allow room for the wicking structure behind the fronting and patches.

The vertical groove 428 of a guide structure can be formed into the outer surface of the caddy 403 between the cavity 280 for mounting the strip-carrying cartridge 190 and the angular portion 405 for the adulteration test apparatus. The groove is slidingly engaged by a corresponding tongue extending inwardly from the vessel inner sidewall similar to one shown in the prior embodiment (228 in FIG. 15).

Figure 17:
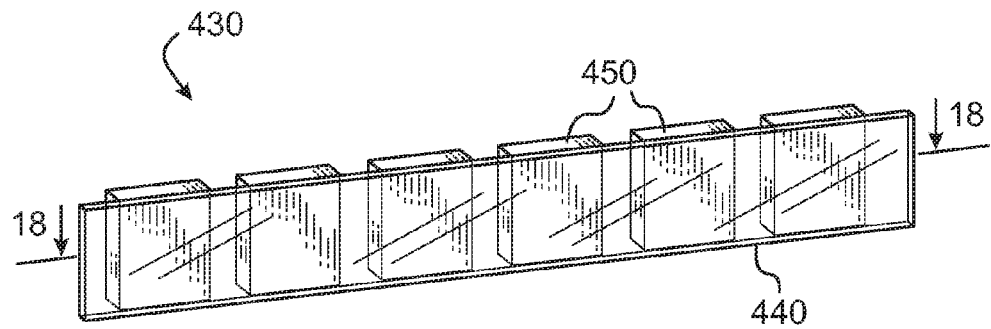
FIG. 17 is a diagrammatic, perspective view of the alternate adulteration test panel of FIG. 16.
Figure 18:
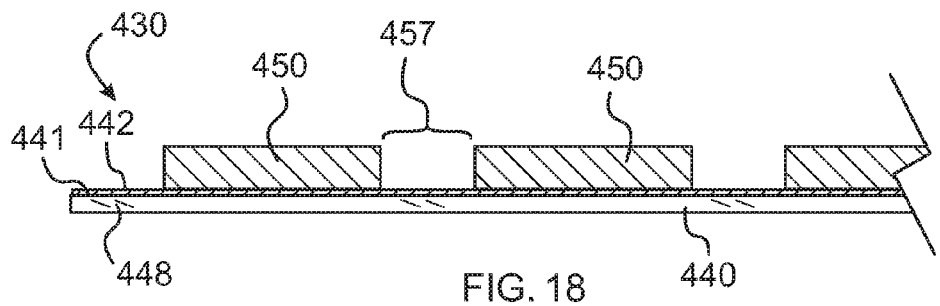
FIG. 18 is a diagrammatic, cross-sectional, partial top view of the adulteration test panel of FIG. 17 taken along line 18-18.

Referring now to FIGS. 17 and 18, the alternate adulteration test panel 430 can include a plurality of individual detector patches 450 each adapted to detect different parameter in the liquid specimen. By changing color, a patch can indicate whether that parameter falls suspiciously outside the normal range for that parameter in the type of specimen being tested. For example, when testing for abused drugs in urine, adulteration parameters can include: concentrations of creatine, nitrite, and glutaraldehyde; the specimen pH, and/or specific gravity; and, the presence of oxidizing agents such as bleach and hydrogen peroxide. Therefore, the number of patches will depend on the number of parameters being scrutinized. For testing for abused drugs using a urine specimen, the number of patches typically range between four and eight patches, and are often six or seven patches.

The patches 450 can be mounted on an oblong translucent fronting 440 made from a strip of transparent sheet material such as clear acrylic plastic. One face 441 of the strip has a layer 442 of adhesive to contact and secure the patches to the strip, and to contact and secure the entire panel to the caddy at the interstices 457 and lateral flaps 448. The adhesive should be chemically compatible with the chemistry being conducted on all of the patches. The fronting can be created from a cut piece of a pressure sensitive adhesive strip material such as 3M 415 acrylic pressure sensitive adhesive strips commercially available from the 3M company of St. Paul, Minn.

Because the color of the patch indicates the result, the patch must be visible to the technician evaluating the test. Therefore the fronting must be translucent and preferably transparent so that the patches are not visibly obscured.

Figure 19:
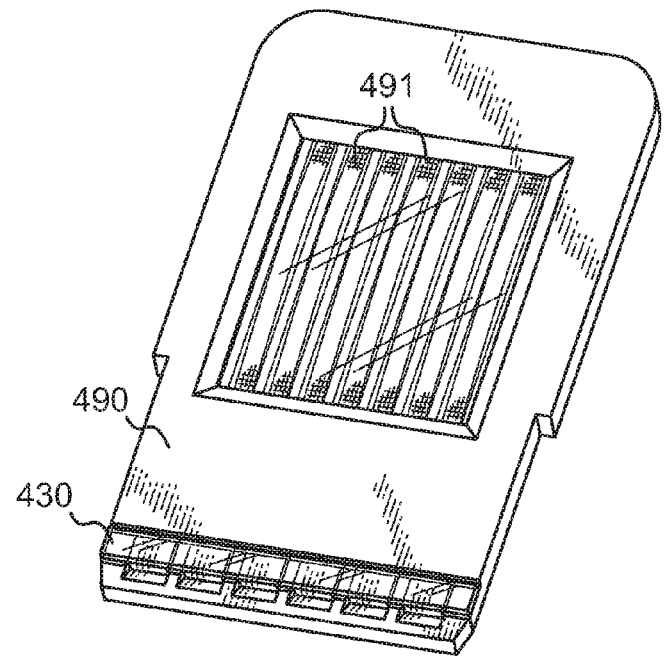
FIG. 19 is a diagrammatic, perspective view of a manually dipped strip-carrying cartridge including an adulteration-type test.

As shown in FIG. 19, the alternate adulteration panel 430 having a transparent adhesive backed fronting can secure adulteration patches to a dipping cartridge 490 similar to the Cipkowski device referenced earlier which carries a number of chromatographic test strips 491. There is a manufacturing cost advantage to providing an adulteration panel which can be used in both an arcuate type cartridge for being mounted either in a cup for non-controlled initiation, or a movable caddy-type, controlled initiation cup as detailed above, or a manual dipping cartridge-type device.

While the exemplary embodiments of the invention have been described, modifications can be made and other embodiments may be devised without departing from the spirit of the invention and the scope of the appended claims.

What is claimed is:

1. An assay device for testing a fluid specimen, said device comprises:
    a vessel defining a first compartment having a top opening and a closed bottom separated along an axis, and said compartment having a given capacity;
    wherein said vessel comprises a translucent wall portion having an inner surface;
    a caddy contained within said compartment;
    wherein said caddy further comprises:
        an internal chamber having an upper opening and a lower opening;
        said lower opening being surrounded by a lower lip; and,
        said caddy being adapted to mount a number of chromatographic test strips on an outer surface of said caddy separated from said internal chamber;
    said caddy being axially translatable within said compartment between a first upper axial position wherein said lower lip is suspended a distance above said closed bottom whereby fluid can flow from said internal chamber to said strips, and a second lower axial position wherein said lower lip is hermetically sealed against said closed bottom whereby fluid cannot flow from said internal chamber to said strips;
    a disableable obstruction preventing movement of said caddy between said first and second axial positions; and,
    a lid removably and hermetically sealing said top opening while said caddy is in either said first or second axial position.

2. The device of claim 1, wherein said caddy further comprises a number of angularly spaced apart channels in said outer surface.

3. The device of claim 1,
    wherein said lower opening is sealed by a frangible barrier.

4. The device of claim 3, which further comprises a projection extending from said closed bottom; said projection being oriented to break said frangible barrier when said caddy is in said second lower axial position.

5. The device of claim 1, wherein said strips are carried within a cartridge insertable in a cavity on said caddy.

6. The device of claim 1, wherein said lid comprises an arcuate bearing surface contacting and driving said caddy from said first upper axial position to said second lower axial position in correspondence to said lid moving axially said distance.

7. The device of claim 6, wherein said arcuate bearing surface comprises a resilient washer hermetically sealing a contact between said arcuate bearing surface and said caddy.

8. The device of claim 1, wherein an axial distance between said first upper axial position and said second lower axial position is between about 3 and 5 millimeter.

9. The device of claim 1, which further comprises an O-ring coursing circumferentially around said outer surface below said upper opening of said caddy, and between said caddy and said vessel for preventing fluid leaking between said channels and said compartment.

10. The device of claim 9, wherein said O-ring is dimensioned to support the weight of said caddy in said first position.

11. The device of claim 1, wherein said lid is shaped and dimensioned to releasably seal said opening and have an annular prominence shaped and dimensioned to be bearingly engage a brim of said caddy.

12. The device of claim 11, wherein said annular prominence is further shaped and dimensioned to contact said caddy in an angularly sliding manner and drive it from said first upper axial position to said second lower axial position while said lid is being screwed completely on said device.

13. The device of claim 1, wherein said caddy is in substantial axial alignment with said compartment.

14. The device of claim 13, which further comprises a guide structure restricting angular movement while allowing axial movement between said caddy and said vessel.

15. The device of claim 2, wherein each of said strips is loaded into an empty one of said number of channels within said caddy.

16. The device of claim 1, wherein said disableable obstruction comprises a cylindrical collar removably positioned on said vessel to prevent axial movement of said lid beyond a defined limit.

17. The device of claim 16, wherein said collar and said lid are co-helically threaded.

18. The device of claim 1, wherein said device further comprises:
    a resilient mat located at said closed bottom of said vessel, said mat being shaped and dimensioned to sealably contact an annular undersurface of said caddy along said lower lip.

* * * * *